United States Patent
Ryan et al.

(10) Patent No.: US 7,016,731 B2
(45) Date of Patent: Mar. 21, 2006

(54) SENSING ARTIFACT REDUCTION FOR CARDIAC DIAGNOSTIC SYSTEM

(75) Inventors: Stephen J. Ryan, Chaska, MN (US); Harold H. Hoium, Eden Prairie, MN (US)

(73) Assignee: Harbinger Medical, Inc., Eden Prairie, MN (US)

( * ) Notice: Subject to any disclaimer, the term of this patent is extended or adjusted under 35 U.S.C. 154(b) by 315 days.

(21) Appl. No.: 10/607,839

(22) Filed: Jun. 27, 2003

(65) Prior Publication Data

US 2004/0054383 A1 Mar. 18, 2004

Related U.S. Application Data

(60) Provisional application No. 60/392,491, filed on Jun. 28, 2002.

(51) Int. Cl.
*A61N 1/365* (2006.01)
(52) U.S. Cl. ....................................................... 607/27
(58) Field of Classification Search .................. 607/5, 607/7, 8, 27, 28; 600/515–523, 18
See application file for complete search history.

(56) References Cited

U.S. PATENT DOCUMENTS

| | | | |
|---|---|---|---|
| 3,805,795 A | 4/1974 | Denniston et al. | |
| 4,522,194 A * | 6/1985 | Normann | 600/18 |
| 4,969,467 A | 11/1990 | Callaghan et al. | |
| 5,117,834 A | 6/1992 | Kroll et al. | |
| 5,555,888 A | 9/1996 | Brewer et al. | |
| 5,694,943 A | 12/1997 | Brewer et al. | |
| 5,735,883 A | 4/1998 | Paul et al. | |
| 5,817,130 A * | 10/1998 | Cox et al. | 607/5 |
| 5,951,484 A | 9/1999 | Hoium et al. | |
| 6,129,678 A | 10/2000 | Ryan et al. | |

FOREIGN PATENT DOCUMENTS

WO    PCT WO 00/76397    12/2000

* cited by examiner

*Primary Examiner*—George Manuel
(74) *Attorney, Agent, or Firm*—Patterson, Thuente, Skaar & Christensen, P.A.

(57) ABSTRACT

Sensing artifacts in cardiac signals picked up by electrical leads are reduced by placing an electrical shunting switch across the conductors of the ECG sensing leads and the stimulation leads that deliver a subthreshold electrical stimulation. In addition, impedance switches are placed in series with the sensing leads. The shunting switches and impedance switches are then manipulated to present cardiac signals that can be analyzed for diagnostic purposes within less than 100 ms from delivery of a subthreshold electrical stimulation.

22 Claims, 5 Drawing Sheets

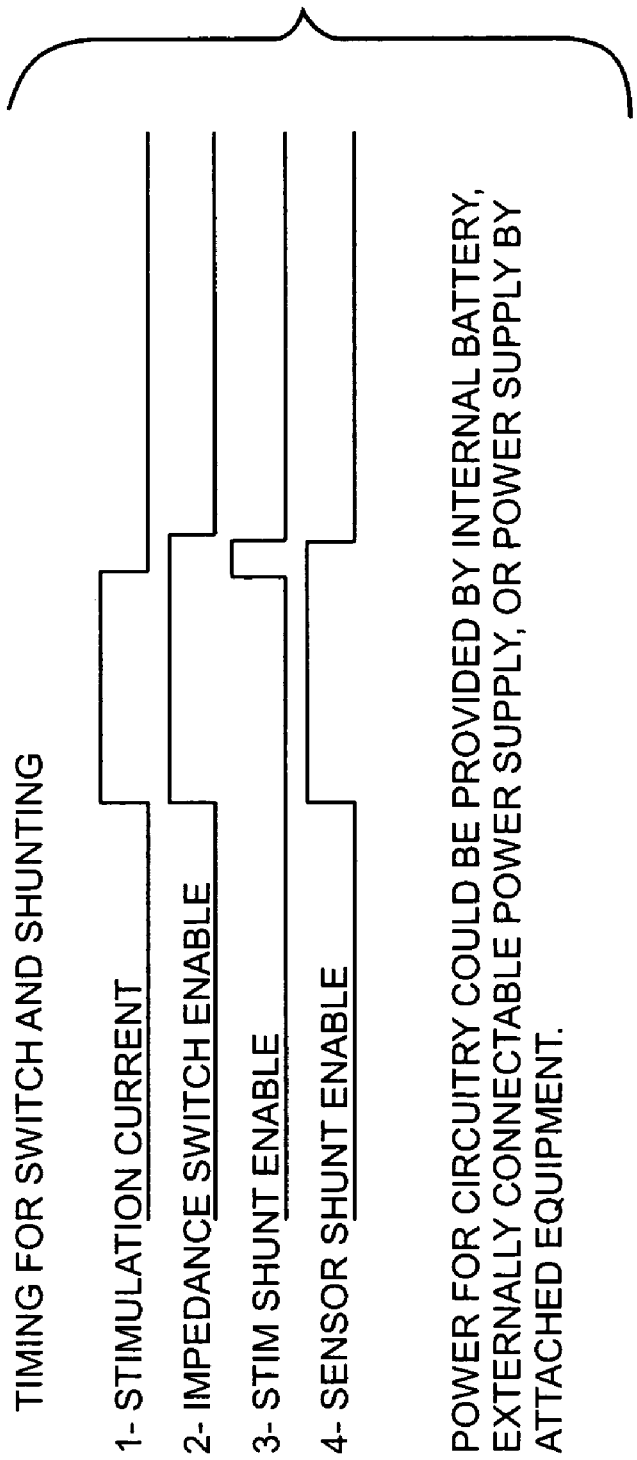

SENSING ARTIFACT REDUCTION FOR CARDIAC DIAGNOSTIC SYSTEM

RELATED APPLICATION

The present application claims priority to U.S. Provisional Application No. 60/392,491 filed Jun. 28, 2002, which is incorporated herein in its entirety by reference.

FIELD OF INVENTION

The invention relates to the detection of patients' susceptibility to cardiac arrhythmias. More particularly, the present invention relates to methods and apparatus for improving the quality of cardiac signals detected for diagnostic purposes.

BACKGROUND OF THE INVENTION

Electrical sensing of cardiac signals is widespread and common in the diagnosis and treatment of cardiac disease. Cardiac signals are sensed in the form of ElectroCardio-Grams (ECG) for diagnostic and monitoring purposes by devices such as conventional ECG strip chart recorders, signal averaged ECG monitors, Holter monitors, vector cardiographs, and a variety of similar devices. Cardiac signals are also sensed by most cardiac stimulation devices that apply electrical energy to the heart for therapeutic purposes, such as defibrillators and pacemakers.

The need to protect the electrical-circuits that sense the cardiac signals from potentially damaging electrical stimulation has long been recognized. Most cardiac stimulation devices, and all implantable cardiac stimulation devices such as implantable cardioverter defibrillators (ICDs) and pacemakers include some form of protection circuitry that can block unintended electrical energy to prevent it from damaging the relatively delicate sensing circuitry.

In addition to the need for protection from the higher therapeutic energy levels applied to the heart, there is a competing need for high sensitivity when sensing cardiac signals in order to closely evaluate the subtle differences between electrical levels created by normal and abnormal heart activity.

Many cardiac devices apply therapeutic electrical energy to the heart and then act to sense the resulting cardiac electrical activity to determine the effect of the therapeutic application. These devices include those used for defibrillation or pacing for example. For these devices, it is not necessary to start sensing immediately after delivery of, electrical energy in order to determine whether the heart is responding appropriately to the delivered therapy. It has generally been considered acceptable, for therapeutic purposes, that the cardiac sensing circuitry only needs to be able to sense the next cardiac event that occurs from 100 to 1500 ms following energy delivery.

In order to best meet these competing needs in the context of cardiac stimulation devices, the dual concepts of shunting and blanking have been developed. Shunting involves inserting switches between the conductors in the leads to the sensing circuitry to shunt or short the two leads together to prevent damage to the sensing circuitry by preventing any electrical energy from getting to the sensing circuitry.

Blanking involves selectively ignoring whatever signals are presented to the cardiac sensing circuitry for a given period of time following delivery of electrical stimulation energy. During the blanking period the sensing circuitry is isolated from cardiac electrical activity and no sensing can take place. As a result, existing cardiac sensing circuitry generally is not designed to allow for effective sensing of cardiac signals during the brief period of less than about 100 milliseconds immediately following delivery of electrical stimulation energy.

Recently, a technique has been developed to improve the ability of physicians to identify patients that are at an abnormally high risk for life-threatening cardiac arrhythmias. This technique, as described in U.S. Pat. Nos. 5,951,484 and 6,129,678, involves analyzing cardiac signals immediately after the application of relatively small levels of electrical stimulation that is below the stimulation threshold of cardiac tissue. During the period of the first 100 ms immediately following delivery of a subthreshold electrical stimulus, it is possible to observe minute electrical phenomenon in the sensed cardiac electrical activity such as the Wedensky phenomena. Conventional cardiac sensing circuitry is not designed to sense signals in this time period. So, the techniques described in these patents incorporate special cardiac sensing circuitry that uses fast recovery amplifiers in order to sense cardiac signals at high levels of sensitivity. Instruments using this approach can discriminate between sensing artifacts and true deviations in cardiac signals even though the cardiac tissue still has a residual electrical charge associated with the delivery of a subthreshold electrical stimulation.

While the technique of analyzing cardiac signals in response to the delivery of subthreshold electrical stimulation has the potential for significant improvement in the ability to determine patients' susceptibility to cardiac arrhythmias, it would be advantageous to be able to make use of these techniques in combination with conventional cardiac sensing circuitry.

SUMMARY OF THE INVENTION

The present invention provides a method and apparatus for reduction of sensing artifacts for cardiac signals sensed for cardiac diagnostic system. Sensing artifacts in cardiac signals picked up by electrical leads are reduced by placing an electrical shunting switch across the conductors of the ECG sensing leads and the stimulation leads that deliver a subthreshold electrical stimulation. In addition, impedance switches are placed in series with the sensing leads. The shunting switches and impedance switches are then manipulated to present cardiac signals that can be analyzed for diagnostic purposes within less than 100 ms from delivery of a subthreshold electrical stimulation.

The timing and application of the present invention is intended to allow the evaluation of cardiac signals very shortly after stimulation energy is applied. By reducing the artifacts present in cardiac signals immediately following delivery of a subthreshold electrical stimulation, the present invention allows for sensing of very low energy cardiac phenomena by conventional cardiac sensing circuitry in the first 100 ms following a subthreshold stimulation. Preferably, the present invention allows for sensing of true cardiac signals by conventional cardiac sensing circuitry within 50 ms following stimulation. Another advantage of the present invention is the ability to reduce artifact stimulation that appears after this time period such as, for example, in the sensing of a T-wave after stimulation of an R-wave.

The system involves the use of shunting and impedance switching techniques in the detection of the direct and immediate response to a subthreshold electrical stimulation. Existing artifact reduction techniques for cardiac sensing circuitry following an electrical stimulation are geared around the detection of a residual state or rhythm following that stimulation. In the case of defibrillation, the therapy is delivered and some time later an evaluation is done to determine if the rhythmic state of the heart had been altered back to a normal sinus rhythm. In the case of pacing, an evaluation of whether there was an effective "capture" of the pacing pulse, is made in order to determine whether there is a need for increased stimulation energy.

In contrast, the present invention involves assessing the patient's immediate response to stimulation and using this diagnostic assessment to determine a patient's susceptibility to future cardiac arrhythmias, as opposed to determining the efficacy of a just delivered therapy. As such, the present invention relates to diagnostic cardiac procedures, and not to evaluating the effectiveness of therapeutic measures.

The present invention may desirably be placed in an adapter inserted between the cardiac leads and a conventional cardiac sensing apparatus, or the present invention can be incorporated directly into a lead assembly that will be plugged into a cardiac sensing apparatus. By incorporating the artifact reduction techniques of the present invention within an adapter or within a lead assembly, the present invention allows the software techniques for analyzing subtle cardiac phenomenon such as the Wedensky effect to be performed on conventional equipment. Preferably, the techniques of the present invention are automatically enabled so as to further enhance the utility and versatility of enabling existing conventional equipment to perform improved cardiac diagnostic techniques.

One embodiment of this invention places a mechanism within an electrical lead set connector that allows the lead set to actively reduce sensing artifacts. This involves placing an electrical shunting switch across the conductors of the stimulating and ECG sensing leads. Additionally, solid state impedance switches are placed in series with the sensing leads. The lead set connector may be a part of the disposable lead, an adapter, or within a cable.

Preferably, the shunt circuit across the stimulation leads automatically activates at the end of the stimulation for a short period of time of less than about 10 ms. This shunting allows residual energy stored on the leads to dissipate through the shunt connection. The impedance switches automatically switch to a high impedance during the application of stimulation energy. This high impedance restricts the flow of energy into the sensing leads. The impedance switches automatically returns to a low impedance following the termination of the shunting of stimulation leads. The shunt circuit across the ECG leads automatically activates during stimulation. Power for the active elements (current detector, shunt, impedance switches) may be via an embedded battery, a separate external power supply, or an additional conductor from the host system. Timing of the shunt and switch activation are provided via a sensitive current sensing circuit in the lead connector which identifies when current is flowing through the stimulation leads.

The present invention enhances the effective performance of the cardiac sensing circuitry in a conventional high resolution ECG system by enabling for faster recovery and sensing following stimulation. By placing the shunt circuit and impedance switches within the lead connector, or adaptor, the use of a conventional ECG amplifier for measuring subthreshold Wedensky phenomena modulation becomes possible.

BRIEF DESCRIPTION OF THE DRAWINGS

FIG. 5 graphically depicts the sequence and timing of the function of the invention.

DETAILED DESCRIPTION OF THE PREFERRED EMBODIMENT

Figure 1:
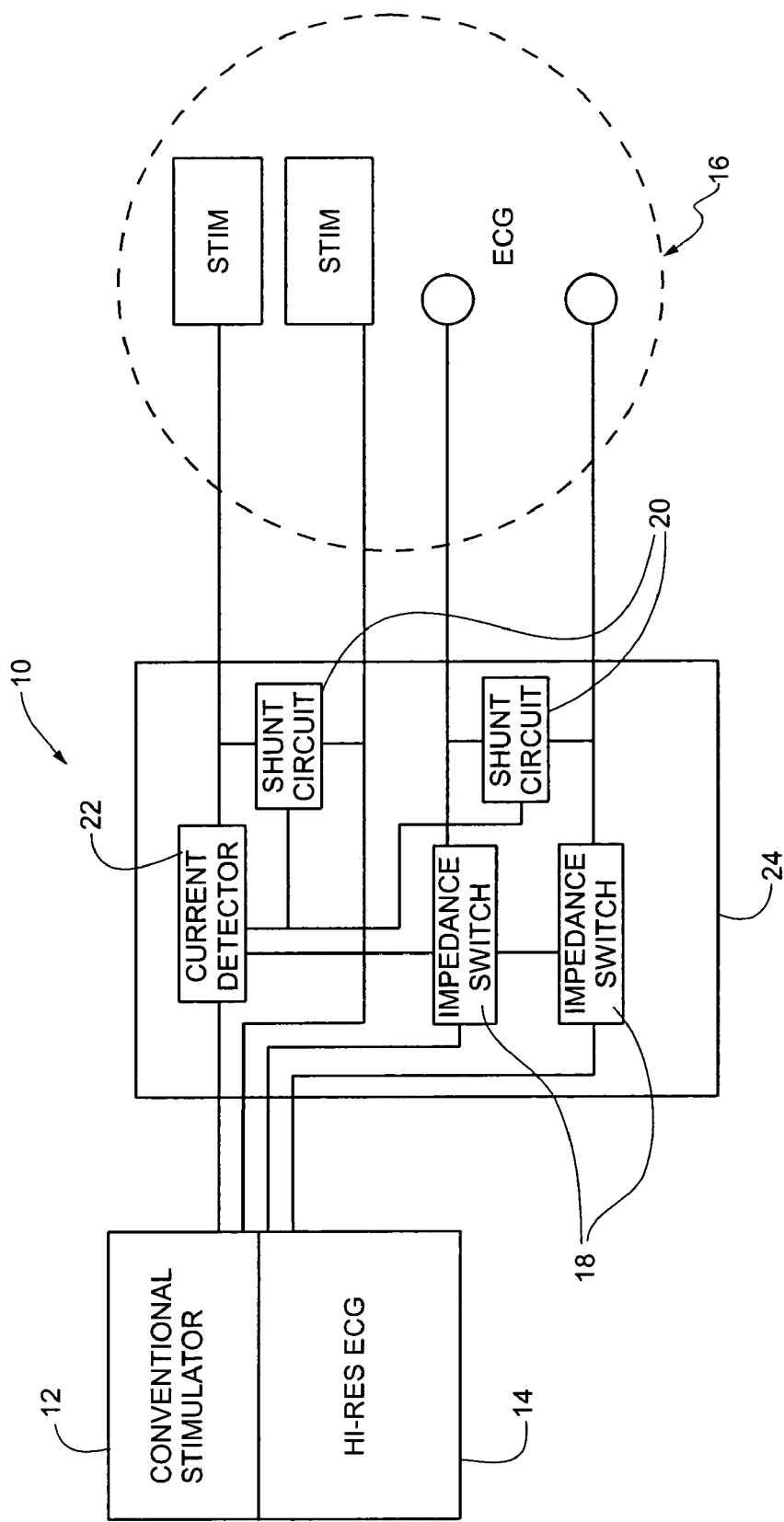
FIG. 1 is a schematic overview of sensing artifact reduction module of the present invention.
Figure 2:
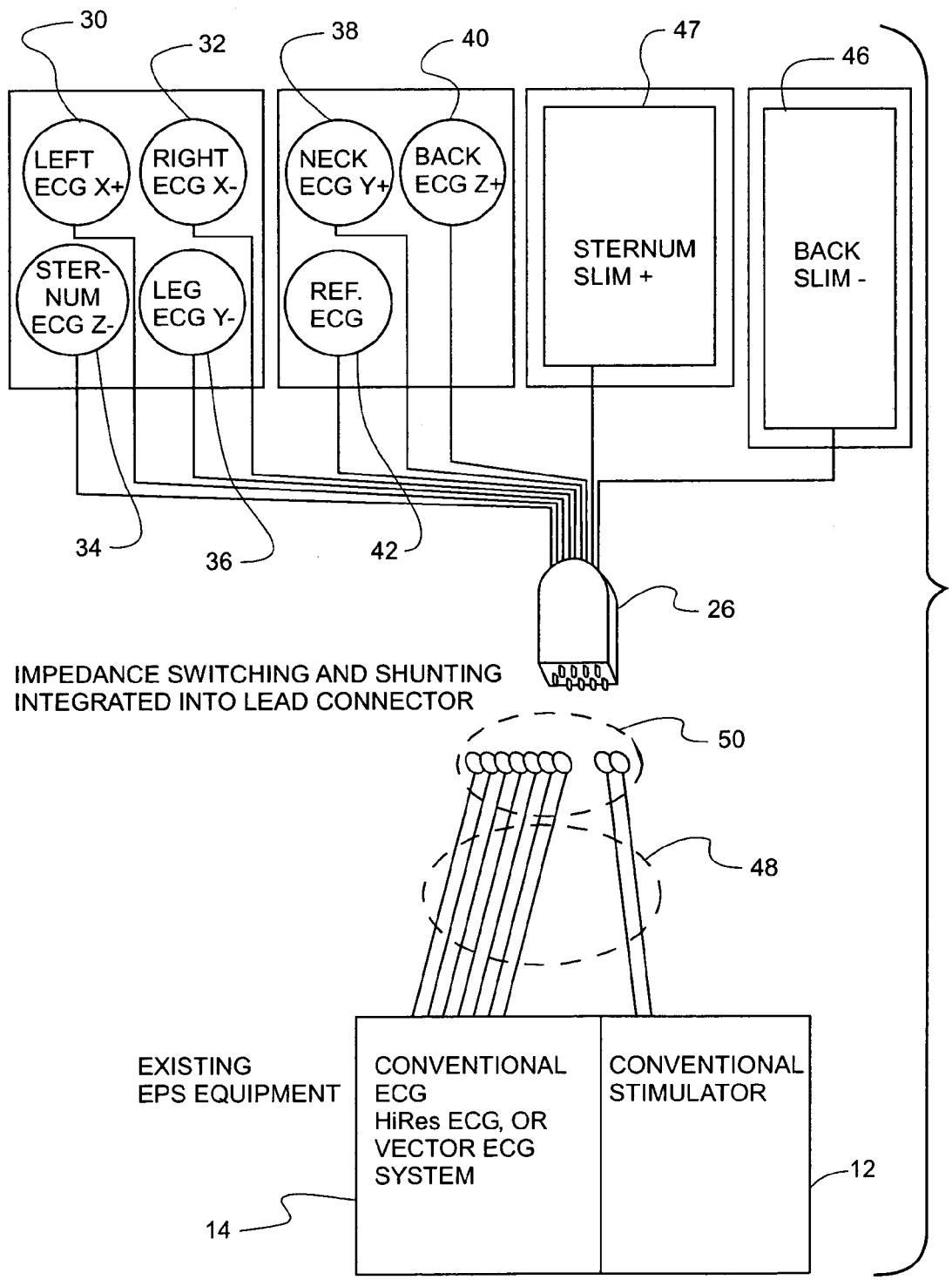
FIG. 2 is a schematic representation of the invention integrated into a lead connector.
Figure 3:
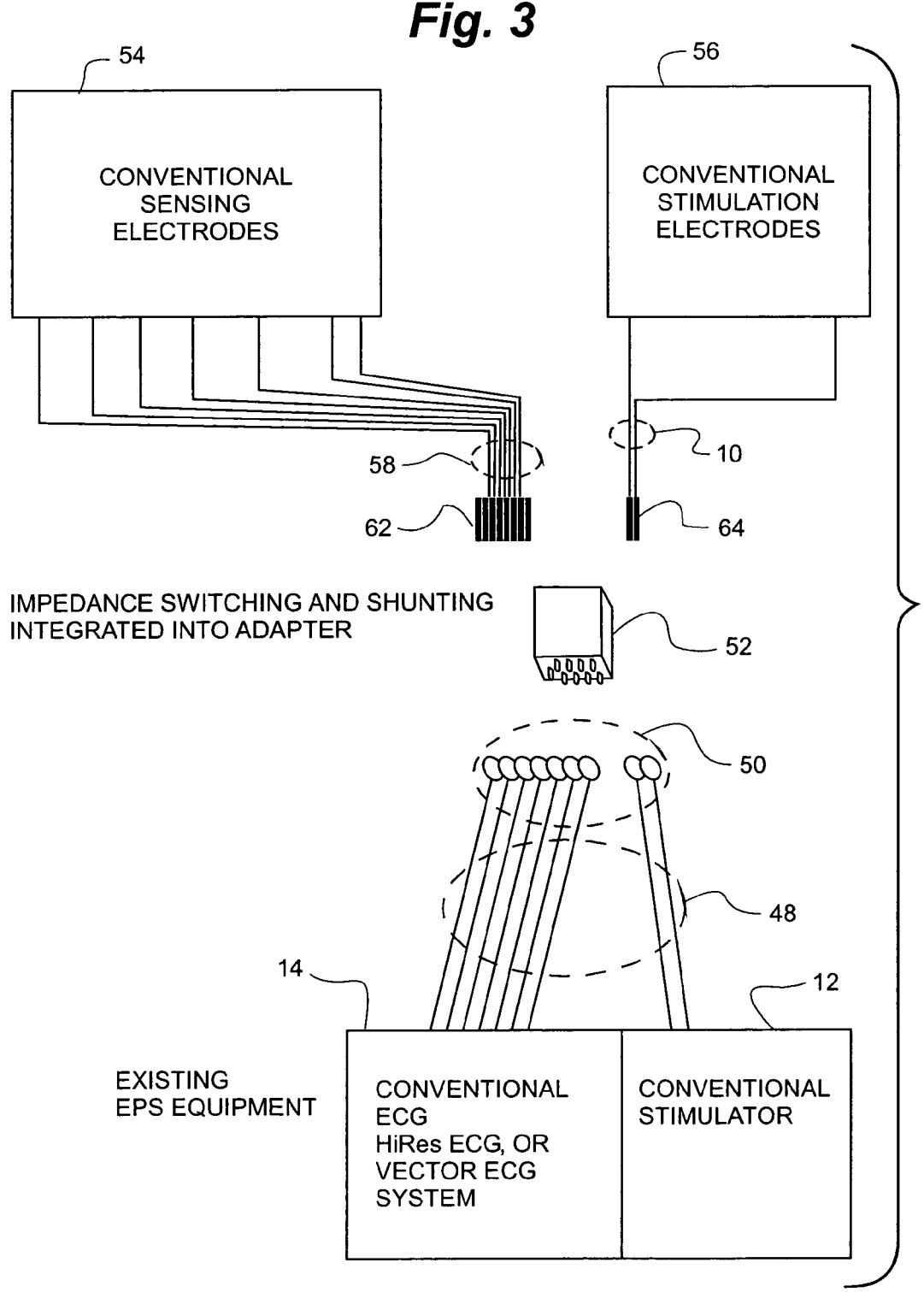
FIG. 3 is a schematic representation of the invention integrated into a separate adapter.

Referring to FIG. 1, the sensing artifact reduction module 10 of the present invention is shown interposed between a conventional stimulator 12, an electrocardiogram (ECG) 14 and electrodes 16. Referring to FIGS. 1, 2 and 3, ECG 14 may include a conventional ECG, a high resolution ECG, a vector ECG system or other like systems. Conventional stimulators 12 are known in the cardiac stimulating and sensing arts.

Sensing artifact reduction module 10 generally includes impedance switches 18, shunt circuits 20, current detector 22 and housing 24.

Referring to FIG. 2, the sensing artifact reduction module 10 is depicted as integrated into lead connector 26. Lead connector 26 is connected to electrodes 16 via a plurality of leads 28. Electrodes 16 include left ECG X positive electrode 30, right ECG X negative electrode 32, sternum ECG Z negative electrode 34, leg ECG Y negative electrode 36, neck ECG Y positive electrode 38, back ECG Z positive electrode 40, reference ECG electrode 42, sternum stimulation positive electrode 44 and back stimulation negative electrode 46. Conventional stimulator 12 and ECG 14 include a plurality of instrument leads 48 and a plurality of instrument terminals 50. Lead connector 26 is adapted to connect to instrument terminals 50.

FIG. 3 depicts the invention integrated into an adaptor 52. Adaptor 52 is configured to be connected to conventional sensing electrodes 54 and conventional stimulation electrodes 56. Conventional sensing electrodes 54 and conventional stimulation electrodes 56 are connected to sensing leads 58 and stimulation leads 60 respectively. Sensing leads 58 and stimulation leads 60 are operably connected to sensing terminals 62 and stimulation terminals 64, respectively Sensing terminals 62 and stimulation terminals 64 are adapted for operable electrical connection to adapter 52. Adapter 52 is further configured for operable electrical connection to instrument terminals 50.

Figure 4:
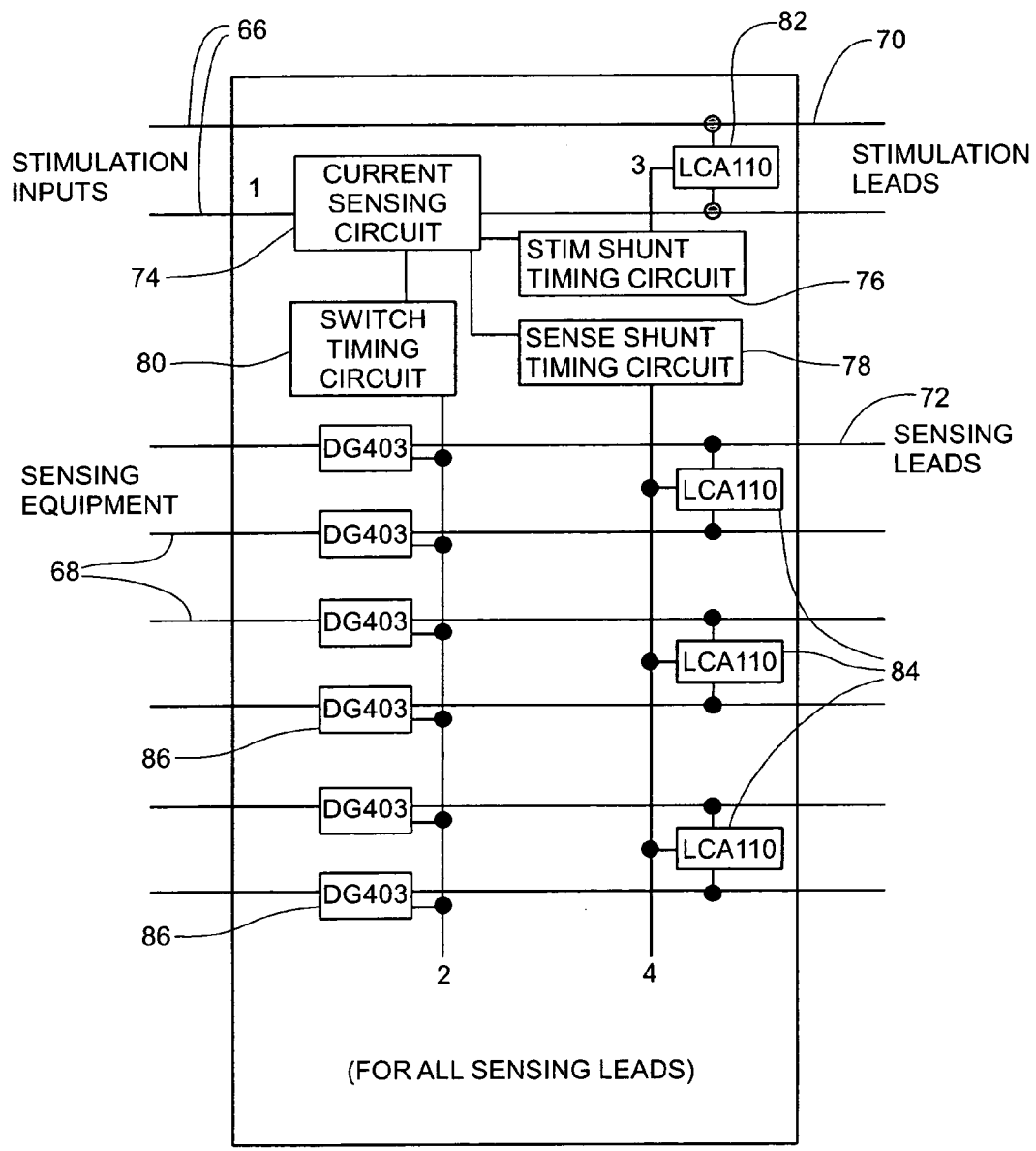
FIG. 4 is a detailed schematic representation of the invention.

FIG. 4 is a detailed schematic of the sensing artifact reduction module 10. Sensing artifact reduction module 10 includes stimulation inputs 66, sensing outputs 68, stimulation lead connections 70 and sensing lead connections 72. Current sensing circuit 74 is operably electrically connected to one of stimulation inputs 66. Current sensing circuit 74 controls stimulation shunt timing circuit 76, sensing shunt timing circuit 78 and switch timing circuit 80.

Current sensing circuit 74 controls stimulation shunt 82 via stimulation shunt timing circuit 76, and also controls a plurality of sensing lead shunts 84 via sensing shunt timing circuit 78 and a plurality of impedance switches 86 via impedance switch timing circuit 80.

Referring to FIG. 5, the sequence and timing of the function of the invention is depicted. As can be seen on line 1, the stimulation current is applied at time T1. At the same time T1 impedance switch 86 enabling is activated. The impedance switches 86 prevent the relatively high stimulation current from feeding back into the delicate sensing equipment thereby preventing potential damage to the sensing equipment. At the same time T1, the sensor shunts are enabled to shunt sensing leads 58 thus providing for rapid dissipation of any charge accumulated on the sensing leads 58. At T2, the stimulation current ends and the stimulation shunts are enabled, thus promptly discharging any residual charge on the stimulation leads. At T3 the impedance switch 18 is disabled, the stimulation shunt 82 is disabled and the sensor shunts 84 are disabled, thus allowing immediate high sensitivity operation of the sensing leads 58 to detect low level electrical activity of the heart.

The present invention may be embodied in other specific forms without departing from the central attributes thereof, therefore, the illustrated embodiments should be considered in all respects as illustrative and not restrictive, reference being made to the appended claims rather than the foregoing description to indicate the scope of the invention.

What is claimed is:

1. A method of reducing sensing artifacts in cardiac electrical activity sensing equipment used in concert with cardiac stimulating equipment comprising the steps of:
   operably electrically connecting an adapter to a conventional cardiac stimulator and an electrocardiograph;
   applying an electrical stimulus to cardiac tissue via a stimulating lead;
   simultaneously enabling an impedance switch operably electrically corrected to a sensing lead to increase the impedance of the sensing lead;
   further simultaneously enabling sensor lead shunts to dissipate any residual charge in the sensing lead;
   thereafter, terminating the electrical stimulus and simultaneously activating stimulation shunts to dissipate residual charge in the stimulation lead; and
   thereafter, simultaneously, disabling the impedance switch and disabling the sensor lead shunts to allow sensing of cardiac electrical activity.

2. The method as claimed in claim 1, further comprising the step of sensing cardiac electrical activity within about one hundred milliseconds after applying the electrical stimulus.

3. The method as claimed in claim 1, further comprising the step of sensing cardiac electrical activity within about fifty milliseconds after applying the electrical stimulus.

4. The method as claimed in claim 1, further comprising the step of incorporating the adapter in a lead connector.

5. The method as claimed in claim 1, further comprising the step of incorporating the adapter into a lead assembly.

6. An adapter for operable electrical connection between a conventional cardiac stimulator having stimulation outputs, cardiac sensing equipment having sensing inputs and a lead set having at least one pair of stimulation leads and at least one pair of sensing leads, the adapter comprising:
   a current sensing circuit interposed between the stimulation outputs and one of the pairs of stimulation leads;
   a switch timing circuit interconnecting the current sensing circuit with an impedance switch;
   a stimulation shunt timing circuit interconnecting the current sensing circuit with a stimulation shunt, the stimulation shunt selectively electrically interconnecting the pair of stimulation leads; and
   a sensing shunt timing circuit interconnecting the current sensing circuit with a sensor shunt.

7. An adapter for operable electrical connection between a conventional cardiac stimulator having stimulation outputs, cardiac sensing equipment having sensing inputs and a lead set having at least one pair of stimulation leads and at least one pair of sensing leads, the adapter comprising:
   a current detector for detecting current at the stimulation outputs;
   a pair of impedance switches interposed between the sensing, inputs and the sensing leads, the impedance switches being operably controlled by the current detector;
   a stimulation shunt circuit for shunting the stimulation leads to dissipate residual electrical charge, the stimulation shunt circuit being operably controlled by the current detector; and
   a sensing shunt circuit for shunting the sensing leads to dissipate residual electrical charge.

8. The adapter as claimed in claim 7, further comprising a switch timing circuit controlled by the current detector for controlling the impedance switches.

9. The adapter as claimed in claim 7, further comprising a sensor shunt timing circuit controlled by the current detector for controlling the sensor shunt circuit.

10. The adapter as claimed in claim 7, in which the adapter is incorporated into a lead connector.

11. The adapter as claimed in claim 7, in which the adapter is incorporated into a lead set.

12. The adapter as claimed in claim 7, in which the adapter is powered by a power source selected from a group consisting of an internal battery, an externally connected power supply, the conventional cardiac stimulator and the cardiac sensing equipment.

13. The adapter as claimed in claim 7, in which the adapter allows the sensing of cardiac electrical activity within about one hundred milliseconds after applying the electrical stimulus.

14. The adapter as claimed in claim 7, in which the adapter allows the sensing of cardiac electrical activity within about fifty milliseconds after applying the electrical stimulus.

15. An adapter for operable electrical connection between a conventional cardiac stimulator having stimulation outputs, cardiac sensing equipment having sensing inputs and a lead set having at least one pair of stimulation leads and at least one pair of sensing leads, the adapter comprising:
   means for detecting current at the stimulation outputs;
   means for selectively switching impedance interposed between the sensing inputs and the sensing leads, the means for selectively switching impedance being operably controlled by the means for detecting current;
   means for shunting the stimulation leads to dissipate residual electrical charge, the stimulation shunting means being operably controlled by the means for detecting current; and
   means for shunting the sensing leads to dissipate residual electrical charge.

16. The adapter as claimed in claim 15, further comprising means for timing the impedance switching controlled by the means for detecting current for controlling the means for selectively switching impedance.

17. The adapter as claimed in claim 15, further comprising means for timing the means for shunting the sensing leads controlled by the means for detecting current.

18. The adapter as claimed in claim 15, in which the adapter is incorporated into a lead connector.

19. The adapter as claimed in claim 15, in which the adapter is incorporated into a lead set.

20. The adapter as claimed in claim 15, in which the adapter is powered by a power source selected from a group consisting of an internal battery, an externally connected power supply, the conventional cardiac stimulator and the cardiac sensing equipment.

21. The adapter as claimed in claim 15, in which the adapter allows the sensing of cardiac electrical activity within about one hundred milliseconds after applying the electrical stimulus.

22. The adapter as claimed in claim 15, in which the adapter allows the sensing of cardiac electrical activity within about fifty milliseconds after applying the electrical stimulus.

* * * * *